US00PP35651P2

(12) United States Plant Patent
Ritchie et al.

(10) Patent No.: US PP35,651 P2
(45) Date of Patent: Feb. 13, 2024

(54) ***PITTOSPORUM* PLANT NAMED 'PITG722'**

(50) Latin Name: *Pittosporum tenuifolium*
Varietal Denomination: PITG722

(71) Applicants: Jack Ritchie, Otane (NZ); Kathy Ritchie, Otane (NZ)

(72) Inventors: Jack Ritchie, Otane (NZ); Kathy Ritchie, Otane (NZ)

( * ) Notice: Subject to any disclaimer, the term of this patent is extended or adjusted under 35 U.S.C. 154(b) by 0 days.

(21) Appl. No.: 18/142,599

(22) Filed: May 3, 2023

(51) Int. Cl.
*A01H 5/00* (2018.01)
*A01H 6/00* (2018.01)

(52) U.S. Cl.
USPC ..... Plt./234

(58) Field of Classification Search
USPC ..... Plt./226, 234
See application file for complete search history.

*Primary Examiner* — Susan McCormick Ewoldt
(74) *Attorney, Agent, or Firm* — Cassandra Bright

(57) ABSTRACT

A new and distinct *Pittosporum* cultivar named 'PITG722' is disclosed, characterized by unique very glossy, green and gold to chartreuse foliage variegation which has been proven stable. Plants are compact, wind resistant, and tolerate low water cultivation. Plants grow rapidly to a mature small size and have been observed frost tolerant to −6° C. Plants are suitable for small gardens, container cultivation and hedging. The new variety is a *Pittosporum*, typically produced as an outdoor ornamental plant.

3 Drawing Sheets

Latin name of the genus and species: *Pittosporum tenuifolium.*
Variety denomination: 'PITG722'.

BACKGROUND OF THE INVENTION

The new cultivar is a product of chance discovery. The new variety was discovered as a naturally occurring whole plant mutation of an unpatented, unnamed variety of *Pittosporum tenuifolium*. The selection was made at a commercial nursery during 2015 in Central Hawkes Bay, New Zealand.

Asexual reproduction of the new cultivar 'PITG722' was first performed at a commercial nursery in Central Hawkes Bay, New Zealand by terminal vegetative cuttings in 2015. Subsequent propagation by cutting and tissue culture has shown that the unique features of this cultivar are stable and reproduced true to type.

The following traits have been repeatedly observed and are determined to be the unique characteristics of 'PITG722'. These characteristics in combination distinguish 'PITG722' as a new and distinct *Pittosporum* cultivar:

1. Wind resistant plants.
2. Observed frost tolerant to −6° C.
3. Low water cultivation.
4. Tidy, compact growth.
5. Small dimensions—good small garden or hedging plant.
6. Fast growth rate.
7. Unique green and gold to chartruese foliage variegation.
8. Undulate leaf margins.
9. Soft foliage (neither rigid nor sharp).
10. Very glossy foliage appearance.

PARENT COMPARISON

Plants of the new cultivar 'PITG722' are similar to the parent in most horticultural characteristics. The new variety, however, differs in the following:

1. The new variety grows to approximately 2 meters high and 1 meter wide; the parent grows to approximately 5 meters high and 2.5 meters wide.
2. The new variety has a more dense growth habit compared to the more open habit of the parent variety.
3. The new variety has green and gold to chartreuse foliage variegation; the parent variety has solid colored foliage.
4. Due to its compact growth the new variety is suitable for container gardening; the parent variety is not suited for container culture.

COMMERCIAL COMPARISON

'PITG722' can be compared to compared to the commercial variety *Pittosporum* 'Tandarra Gold', unpatented. Plants of 'Tandarra Gold' are similar to plants of 'PITG722' in most horticultural characteristics, however, plants of 'PITG722' differ in the following:

1. The new variety grows to approximately 2 meters high and 1 meter wide; this comparator grows to approximately 3 meters high and 2 meters wide.
2. The new variety grows more rapidly to mature size than this comparator.
3. The new variety has green and gold to chartreuse foliage variegation; this comparator has an olive green and lemon-yellow variegation.

'PITG722' can be compared to compared to the commercial variety *Pittosporum* 'Limelight', unpatented. Plants of 'Limelight' are similar to plants of 'PITG722' in most horticultural characteristics, however, plants of 'PITG722' differ in the following:

1. The new variety grows to approximately 2 meters high and 1 meter wide; this comparator grows to approximately 3 meters high and 2 meters wide.
2. The new variety has soft foliage; foliage of this comparator is firmer, nearly rigid.

3. The new variety has green and gold to chartreuse foliage variegation; this comparator has mid-green and dull gold variegation.
4. Foliage of the new variety is very glossy; foliage of this comparator is matte.

'PITG722' can be compared to compared to the commercial variety *Pittosporum* 'Mellow Yellow', unpatented. Plants of 'Mellow Yellow' are similar to plants of 'PITG722' in most horticultural characteristics, however, plants of 'PITG722' differ in the following:

1. The new variety grows to approximately 2 meters high and 1 meter wide; this comparator grows to approximately 3.5 meters high and 1.5 meters wide.
2. The new variety has green and gold to chartreuse foliage variegation; this comparator has mid-green and butter-yellow variegation.

BRIEF DESCRIPTION OF THE PHOTOGRAPHS

The accompanying drawings drawing in FIG. 1 illustrates in full color a typical plant of 'PITG722' grown outdoors in Dayton, OR. This plant is approximately 18 months old, in a 3-gallon pot.

Figure 1:
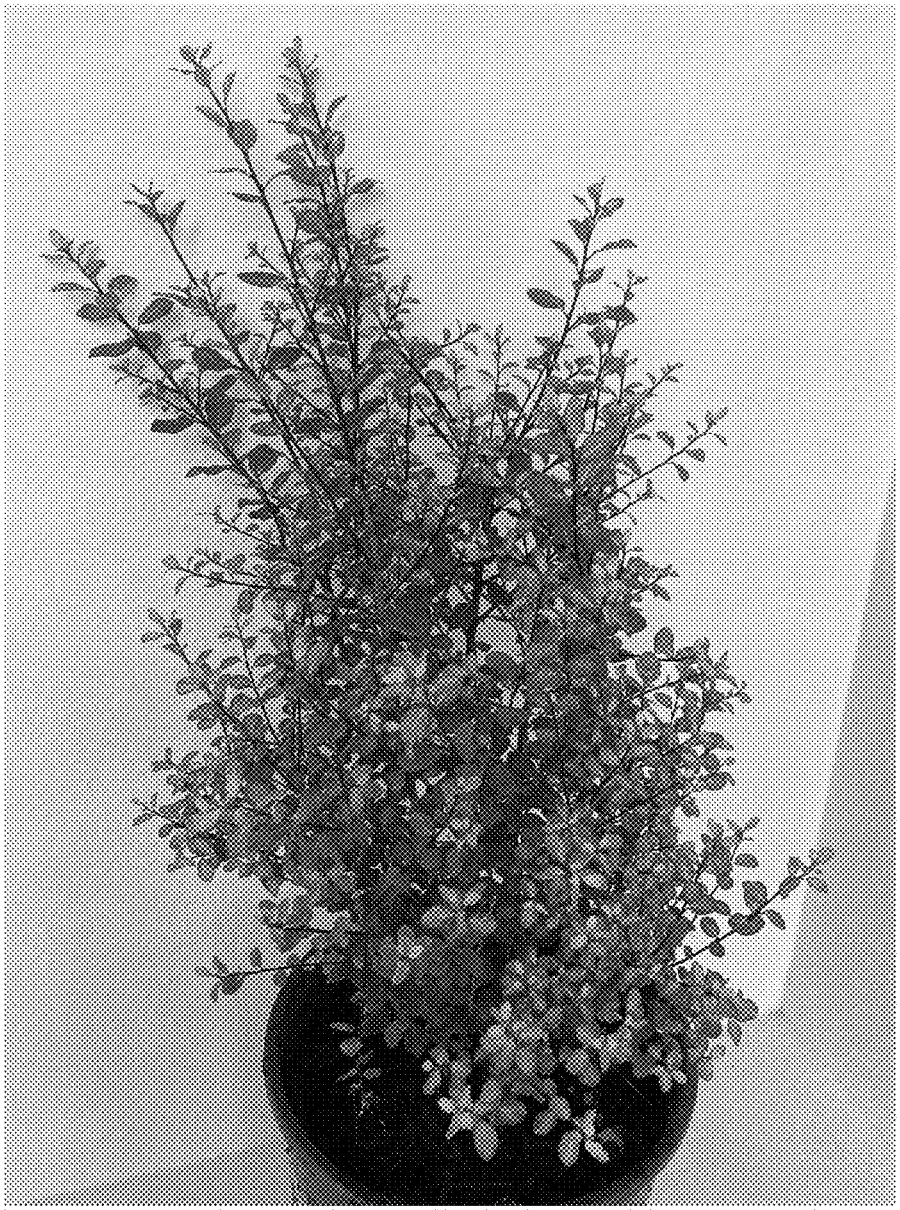
Figure 2:
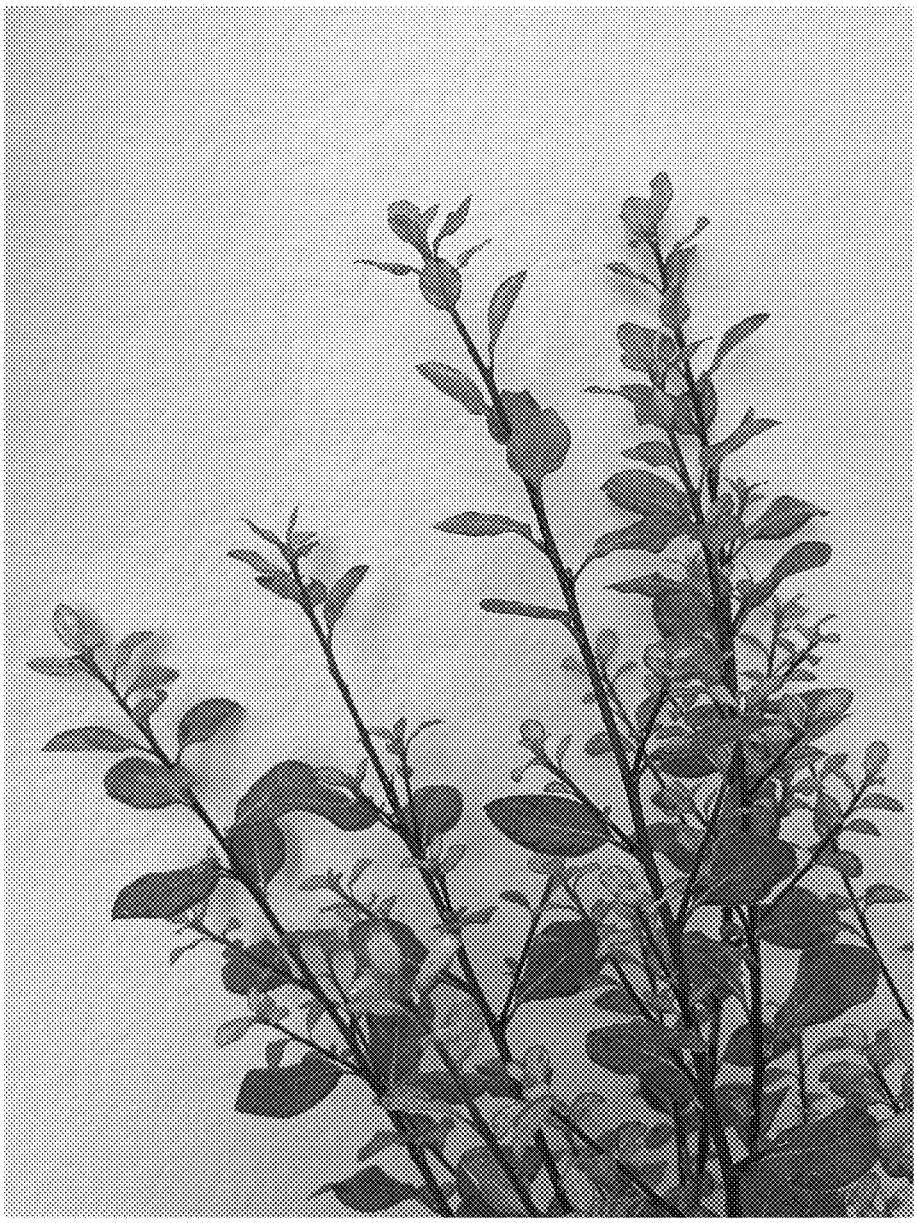
FIG. 2 illustrates multiple stems of new growth of the new variety.
Figure 3:
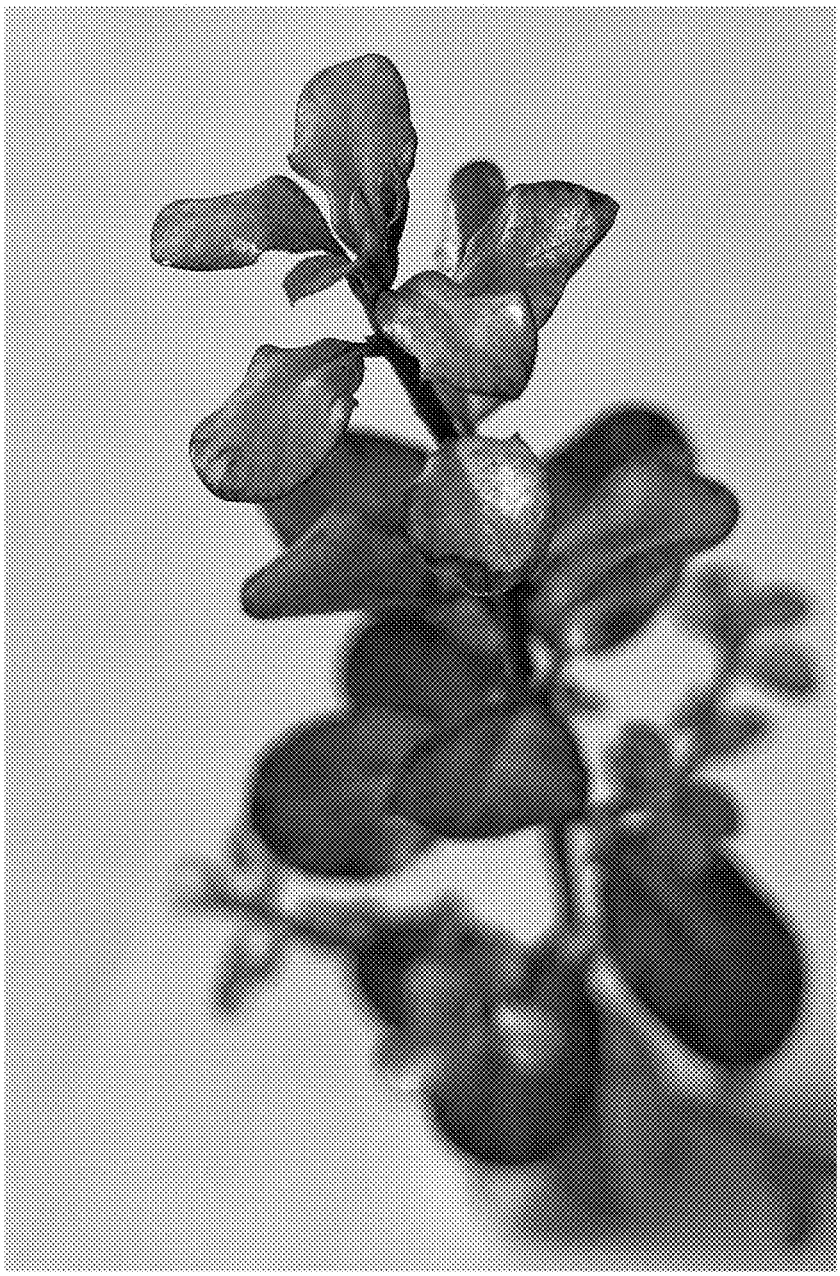
FIG. 3 is a close-up view of young foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'PITG722' plants grown outdoors in Dayton, OR. Temperatures ranged from about −2° C. to 8° C. at night to 5° C. to 28° C. during the day. No artificial light, photoperiodic treatments were given to the plants. Measurements and numerical values represent averages of typical plant types.

Botanical classification: *Pittosporum tenuifolium* 'PITG722'.

PROPAGATION

Type of propagation typically used: Semi-hardwood cuttings taken in late summer/early fall.

Time to produce a rooted cutting: 5 to 6 months to produce a 3-inch liner.

Root description: Very thin, dense, fibrous, not fleshy, freely branching. New roots colored near RHS Yellow-White 158D. Older roots colored near Grey-Brown 199D.

PLANT

Growth habit: Dense, evergreen, upright shrub.
Age of plant described: 18 months.
Container size: 3-gallon.
Overall plant shape: Dense, erect.
Growth habit: Freely branching.
Plant spread: 35 cm.
Plant height: 55 cm in second year.
Growth rate: Rapid.
Plant vigor: Good.

Branching description: Densely branched. About 10 to 12 primary branches near base of plant. Each primary branch has 3 to 4 main lateral branches. Main lateral branches densely branched with additional laterals. When pinched on average 3 new lateral branches emerge, occurring at acute angles, between 15° to 45°.

Primary branches:

*Length*.—Average range 20 to 30 cm, this varies based on pruning or pinching.
*Diameter*.—5 mm.
*Color*.—New growth: Near RHS Greyed-Purple 187A. Old growth: Near RHS Greyed-Purple N187C.
*Shape*.—Round.
*Strength*.—Moderate, neither brittle nor very flexible.
*Aspect angle*.—Acute and straight.
*Texture*.—New growth lightly pubescent. Mature growth smooth with lenticels.
*Lenticels*.—Density: About 10 per 1 cm linear stem. Shape: Round Size: About 0.8 mm in diameter. Color: Near White N155D.

Internode length: Average range 1 to 2.1 cm.
Bark peel: Not observed.

FOLIAGE

Leaf:

*Arrangement*.—Alternate.
*Average length*.—1.8 to 2.4 cm.
*Average width*.—1.3 to 1.5 cm.
*Shape of blade*.—Obovate.
*Apex*.—Acute.
*Base*.—Broad attenuate.
*Margin*.—Entire and undulate.
*Aspect*.—Young foliage undulate; mature foliage very slightly undulate and slightly curved downward.
*Texture of top surface*.—Smooth.
*Texture of bottom surface*.—Smooth.
*Appearance of top surface*.—Very glossy.
*Appearance of bottom surface*.—Matte to slightly glossy.
*Color*.—Newest emerging foliage upper side: Near RHS Yellow-Green 151B, base and margins lightly flushed Yellow-Green 144A. Lower ⅓ of center vein colored near Red-Purple 59A. Veins near margin colored near Red-Purple 59B. Very thin marginal coloration near 59A. Newest emerging foliage upper side: Near RHS Yellow-Green 151B, base and margins lightly flushed Yellow-Green 144A. Lower ⅓ of center vein colored near Red-Purple 59A. Veins near margin colored near Red-Purple 59B. Very thin marginal coloration near 59A. Young foliage upper side: Near RHS Yellow-Green 146B. Irregular blotching near Green 137A along margin. Very faint irregular flushing near Red-Purple 59A. Young foliage under side: Near RHS Yellow-Green 152B. Irregular blotching near Green 137A along margin. Mature foliage upper side: Near RHS Green 137A. Irregular blotching along margin Green 139A. Irregular blotching and flushing near Greyed-Purple 187A throughout leaf blade, covering about 5 to 10% of blade. Mature foliage under side: Near RHS Green 137C. Irregular blotching along margin Green 137A. Irregular blotching and flushing near Greyed-Purple 187A throughout leaf blade, covering about 5% of blade. Venation: Type: Pinnate. Newest emerging foliage venation color upper side: Near RHS Yellow-Green 151C. Lower ⅓ of center vein colored near Red-Purple 59A. Veins near margin colored near Red-Purple 59B. Newest emerging foliage venation color under side: Near RHS Red-Purple 59B. Young foliage venation color upper side: Near RHS Yellow-Green 151D. Faint flushing on lowest part of center vein near Red-Purple 59B. Young foliage venation color under side: Near RHS Yellow-Green 151D, lower 20% flushed Red-purple 59B. Mature foliage venation color upper side: Near RHS Yellow-Green 151D. Mature foliage venation color under side: Near RHS Yellow-Green 145C.

*Petiole*.—Length: 3 to 4 mm. Diameter: 1 to 2 mm. Color: Upper: Near Red-Purple 59A. Oldest leaves Yellow-Green 145C lightly flushed 59A. Lower: Near Red-Purple 59B.

FLOWER

Not observed to date.

REPRODUCTIVE ORGANS

Not observed to date.

OTHER CHARACTERISTICS

Disease resistance: Neither resistance nor susceptibility to normal diseases and pests of *Pittosporum* have been observed.

Drought tolerance and cold tolerance: Tolerates temperatures from approximately 0° C. to Fruit/seed production: Not observed.

What is claimed is:

1. A new and distinct cultivar of *Pittosporum* plant named 'PITG722' as herein illustrated and described.

* * * * *